(12) United States Patent
Krishnan et al.

(10) Patent No.: US 8,993,312 B2
(45) Date of Patent: Mar. 31, 2015

(54) BIO-MATRIX STRETCHER

(75) Inventors: Ramaswamy Krishnan, Cambridge, MA (US); Chan Young Park, Cambridge, MA (US); Jeffrey Fredberg, Sharon, MA (US); Fei Liu, Warwick, RI (US); Justin Mih, Mission Hill, MA (US); Daniel Tschumperlin, Norfolk, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1130 days.

(21) Appl. No.: 12/675,882

(22) PCT Filed: Aug. 28, 2008

(86) PCT No.: PCT/US2008/010216
§ 371 (c)(1),
(2), (4) Date: Jan. 6, 2011

(87) PCT Pub. No.: WO2009/032174
PCT Pub. Date: Mar. 12, 2009

(65) Prior Publication Data
US 2011/0091922 A1    Apr. 21, 2011

Related U.S. Application Data

(60) Provisional application No. 60/969,104, filed on Aug. 30, 2007, provisional application No. 60/970,778, filed on Sep. 7, 2007.

(51) Int. Cl.
| | | |
|---|---|---|
| C12Q 1/02 | (2006.01) |
| C12M 1/34 | (2006.01) |
| C12N 5/00 | (2006.01) |
| C12M 1/32 | (2006.01) |

(52) U.S. Cl.
CPC ............ *C12N 5/0068* (2013.01); *C12M 23/12* (2013.01); *C12N 2533/30* (2013.01)
USPC .................. 435/288.7; 435/305.1; 435/305.3; 435/375; 435/401

(58) Field of Classification Search
CPC ............................ C12M 23/12; C12N 5/0068
USPC ............. 435/289.1, 305.1, 305.2, 305.3, 375, 435/401
See application file for complete search history.

(56) References Cited

U.S. PATENT DOCUMENTS 4,839,280 A * 6/1989 Banes ........................ 435/305.2
5,106,743 A * 4/1992 Franzblau et al. ............ 435/397
(Continued)

*Primary Examiner* — Nathan Bowers
*Assistant Examiner* — Gautam Prakash
(74) *Attorney, Agent, or Firm* — Mintz Levin Cohn Ferris Glovsky and Popeo, P.C.

(57) ABSTRACT

Embodiments provide techniques for measuring and characterizing the dynamics of cell traction forces. Tunable elastic gel substrates can be disposed in multi-well plates. The gels can be of a uniform predetermined thickness. A multi-well plate can be loaded with gels of different shear moduli. An array of punch indenters can be attached to a loading platen such that the each indenter is aligned to a gel substrate. The indenters can apply tensile or compressive strains to the gel substrates. The magnitude, duration, and frequency of the strain can be controlled by a motor assembly coupled to a control system. The apparatus can be disposed in an incubator for long term cell culture experiments. The cell culture can be observed while a strain is applied. A ring-shaped indenter can be mounted on a microscope, coaxial to the objective lens, and lowered by a calibrated amount onto the underlying gel.

24 Claims, 13 Drawing Sheets

(56) References Cited

U.S. PATENT DOCUMENTS

| | | | |
|---|---|---|---|
| 5,217,899 A | | 6/1993 | Shapiro et al. |
| 5,348,879 A | * | 9/1994 | Shapiro et al. .............. 435/375 |
| 5,706,696 A | | 1/1998 | Wagner |
| 6,037,141 A | | 3/2000 | Banes |
| 6,057,150 A | * | 5/2000 | Lee et al. .................. 435/288.3 |
| 6,586,235 B1 | | 7/2003 | Banes |
| 7,160,687 B1 | | 1/2007 | Kapur et al. |
| 2006/0035325 A1 | | 2/2006 | Crabtree et al. |
| 2006/0110822 A1 | | 5/2006 | Robbins et al. |
| 2006/0129327 A1 | * | 6/2006 | Kim et al. ..................... 702/19 |
| 2007/0128174 A1 | | 6/2007 | Kleinsek et al. |

* cited by examiner

BIO-MATRIX STRETCHER

CROSS-REFERENCE TO RELATED ACTIONS

This application is a national stage entry of International Application Number PCT/US2008/010216, filed Aug. 28, 2008, which claims the benefit of U.S. Provisional Application No. 60/970,778 filed Sep. 7, 2007, and claims the benefit of U.S. Provisional Application No. 60/969,104, filed on Aug. 30, 2007.

GRANTS

The government has certain rights to the present invention under contract NIH HL-82856, GM-073628.

BACKGROUND

The physical environment of a living cell acutely determines its ability to proliferate, metabolize, differentiate and remodel. On the one hand, living cells specify lineage and express different phenotypic and physical states with extreme responsiveness to stiffness of their underlying matrix, while on the other, cell stretch, especially as occurs in cells resident in heart, lung, muscle, and gut, is a potent biological stimulus and regulator of tissue and cell size, structure and composition. In general, however, it has not been possible to reproduce both of these aspects of a cell's in-vivo microenvironment, viz. underlying substrate stiffness and cell stretch, within an in-vitro culture.

Techniques have been previously developed in order to reproduce cell stretch within in-vitro cultures. These methods may be broadly classified into the following categories: stretching the adherent cell's underlying substrate, applying hydrostatic pressure within the cell culture chamber, prescribing shear stresses via fluid flows over the adherent cells, applying localized loads using magnetic microbeads, microneedles, AFM cantilevers, micropipettes and optical tweezers, and micropipette and microplate manipulations of cell volume. Some of these techniques have been commercialized and used in biological research (e.g. Flexcell International, STREX from B-Bridge International).

The prior art systems, however, have generally ignored the role of underlying substrate stiffness, by culturing cells on substrates whose stiffness ($\sim 10^9$ Pa) is several orders of magnitude greater than that of the adherent cell. In general, in addition to mechano-sensitivity to external loads, diverse cell types also sense and respond to stiffness of their extra-cellular matrix by modulating their adhesions, shape, contractility, cytoskeletal structure and overall cell state. For example, when cultured on soft matrices (100 to 1000 Pa) that mimic stiffness of brain tissue, stem cells expressed a neurogenic phenotype. When cultured on intermediate stiffness substrates (8000-17000 Pa) resembling the stiffness of muscle, the stem cells expressed a myogenic phenotype. Also, when cultured on even stiffer substrates (25000-40000 Pa) that approximates the stiffness of collagenous bone, stem cells commit to an osteogenic phenotype. Some studies have reported considerable implications of local matrix stiffness on cell differentiation, proliferation, spreading and migration, mechanotransduction, osteogenesis and several disease processes.

Accordingly, the inventions described herein overcomes methodological limitations in the described prior art techniques that either culture cells on soft matrices that are static and passive, or on exceedingly stiff, dynamic substrates.

SUMMARY

In accordance with implementations of the invention, one or more of the following capabilities may be provided. Aspects of a cells in-vivo microenvironment within an in-vitro culture can be reproduced. High-throughput applications in cell cultures, stem cell therapy, drug discovery and traction microscopy, can be realized. Cell-contractile forces in response to a stretch can be quantified and correlated with cell-mechanical properties such as contraction, spreading, crawling and invasion. Loading plates with multiple well can include tunable gels with different stiffness moduli.

Multiple stiffness gels, varying in orientation, can be casted and derivatized in a 96-well glass-bottom plate. Stiffness-dependent biology can be assessed in a high-throughput manner and subject to a standard 96-well plate assay, including but not limited to, cell proliferation, apoptosis, signaling events, and detection of soluble and insoluble factors. Cells grown in the multiple stiffness plate can be fixed and immunologically stained, or isolated for gene expression and protein analysis. Attachment-dependent cell types can be conceivably studied, including fibroblasts, smooth muscle, endothelial, epithelial, tumor, osteoid, and neuronal. The plate can serve as a tool to direct the differentiation of adult or embryonic stem cells.

The devices and methods described herein are useful to program or reprogram embryonic and/or adult stem cells, e.g., the latter being obtained from normal or tumor-derived tissue. The cells are cultured in the chamber and subjected to variations is stiffness of the substrate and/or to physical changes, e.g., stretching forces, exerted by the device. The substrate characteristics or applied physical forces, e.g., compression or stretching, drive or induce differentiation, dedifferentiation, programming, or reprogramming of the cells into cells characterized by a desired phenotype. For example, the application of a stretching force to a stem cell, e.g., an embryonic stem cell or a mesenchymal stem cell obtained from bone marrow or other sources, induce differentiation of the stem cell into a cardiac myocyte or vascular smooth muscle cell. Reprogrammed stem cells are identified by their behavior (e.g., movement or lack thereof), physical state of the cytosol, appearance, change in gene/protein expression, or elaboration of intracellular or secreted factors, among other parameters. The methods and imaging systems are used to monitor characteristics of cells and identify/screen for cells of a desired phenotype, e.g., cells at a desired state of differentiation or "sternness", e.g., phenotype as a response to variations in changes of stiffness of culture substrate and/or stretching forces applied to a cell or plurality of cells. The methods include non-invasive, non-perturbing, automatable, and quantitative methods and are applied to the examination of cells such as adult or embryonic stem cells as well as differentiated cells of all phenotypes and to cells at various stages of differentiation. Viability, sternness, or plasticity of the cell, in response to the culture environment or physical stresses to which the cell or cells are exposed are monitored and quantified at various points during culture, as preserved/fixed, or in real time.

The invention also encompasses a method for altering the structure or morphology of a cell, e.g., by distorting or stretching the cell. The method is carried out by providing a cell on a cell island disposed on a tunable elastic substrate and applying a force to the tunable elastic substrate with a ring-shaped punch indenter with an inner diameter that is larger than the size of the cell island.

The method is applicable to alter a physical or physiological property of any cell. For example, the application of force induces an alteration in cytoskeletal structure and stiffness by inducing a rapid fluidization followed by slow solidification. Alternatively, the application of force or periodic application induces a functional change in the cell, e.g., differential gene expression or protein production. For example, the cell is of a cell type that is subjected to stretching forces in vivo, e.g., a lung cell, heart cell, or cell of the gastrointestinal tract. The cell is a muscle cell such as a skeletal muscle cell, or smooth muscle cell, cardiac muscle cell. Alternatively, the cell is a fibroblast or endothelial cell.

The devices described herein, e.g., those comprising a ring-shaped punch-indenter and a cell culture chamber with an elastic substrate coated with type I collagen, were used to impose graded biaxial stretches upon an isolated cell. Dynamic traction microscopy was used to track cell tractions. Prompt CSK fluidization and slow resolidification mirrored underlying changes in cell tractions, establishing inextricable linkage between the abilities of the CSK to deform, remodel, and contract.

Optionally, the surface of the substrate may be derivitized with other extracellular matrix proteins such as fibronectin and laminin. These methods are applicable to culturing cells such as those used in tissue grafts and reproducing the in vivo environment to which they are eventually engrafted, e.g., beating heart, respirating lung, stomach or intestinal tissue subject to peristalsis. For example, the methods can be used to create a pulsatile environment for the creation of cardiac cells.

In general, in an aspect, the invention provides an apparatus including a well, a tunable elastic substrate disposed within the well, a cell plating area disposed on the tunable elastic substrate, and a ring-shaped punch indenter with an inner diameter that is larger than the size of the cell plating area, and an outer diameter that is smaller than the diameter of the well, wherein the ring-shaped punch is configured to apply a force to the tunable elastic substrate.

Implementations of the invention may include one or more of the following features. At least one motor assembly operably coupled to the ring-shaped punch and can be configured to move the ring-shaped punch within well. The ring-shaped punch can be configured to move vertically with respect to the tunable elastic substrate. The ring-shaped punch can be configured to move horizontally with respect to the tunable elastic substrate. The well can include one or more wells and the ring-shaped punch indenter can includes one or more ring-shaped punch indenters such that each indenter is disposed within each well. The well can be a 96-well plate and the ring-shaped punch indenter can comprise 96 ring-shaped punch indenters such that each indenter is disposed within each of the wells. Each of the wells can include a tunable elastic substrate disposed within the well. The tunable elastic substrate in a well can be of a first thickness, and the tunable elastic substrate in another well can be of a second thickness. The tunable elastic substrate in a first well can be a first stiffness, and the tunable elastic substrate in a second well can be a second stiffness. A programmable control system can be configured to control the at least one motor.

In general, in another aspect, the invention provides a dynamic traction microscopy system including an elastic substrate, a cell plating area disposed on the elastic substrate, a microscope, and a ring-shaped indenter, with an inner diameter greater then the size of the cell plating area, disposed coaxial to the objective lens of the microscope, such that the ring-shaped indenter is configured to exert a strain on the elastic substrate.

Implementations of the invention may include one or more of the following features. At least one motor assembly can be operably connected to the ring-shaped indenter. A control system can be configured cause the ring-shaped indenter to apply and remove the strain on the elastic substrate. The profile of the ring-shaped indenter can be configured to apply a directional strain on the elastic substrate.

In general, in another aspect, the invention provides a method to observe changes in the traction force a cell exerts upon a tunable elastic matrix, including disposing a tunable elastic gel substrate into a well, incorporating an extracellular ligand onto the gel, placing a cell culture in a circular island on the gel, and applying a strain to the gel with a ring-shaped indenter, such that the inner diameter of the indenter is larger than the diameter of the circular island and the outer diameter of the indenter is less then the diameter of the well.

Implementations of the invention may include one or more of the following features. The magnitude of the strain applied to the gel can be controlled. The duration and frequency of the strain applied to the gel can be controlled. The cell culture on the gel can be observed with a microscope while gel is under strain. The method can also include reducing the strain on the gel, and observing the cell culture on the gel with a microscope.

In general, in another aspect, the invention provides a method for altering the structure or morphology of a cell, including providing a cell on a cell island disposed on a tunable elastic substrate and applying a force to the tunable elastic substrate with a ring-shaped punch indenter with an inner diameter that is larger than the size of the cell island.

Implementations of the invention may include one or more of the following features. The cell can be a lung cell, heart cell, or cell of the gastrointestinal tract. The cell can be a muscle cell. The muscle cell can be a skeletal muscle cell or smooth muscle cell. The cell can be a fibroblast or endothelial cell. The substrate can include an extracellular matrix protein. The application of force can induce an alteration in cytoskeletal fluidization or solidification.

Also within the invention is a method of simulating a physiological growth condition by disposing a cell in the device or apparatus. The invention also includes a method to observe changes in the fraction force a cell exerts upon a tunable elastic matrix by viewing a cell with the device or apparatus. For example, the cell is a cardiovascular, gastrointestinal, kidney, genitourinary, musculoskeletal, nervous system, oral, breast, periodontal, or skin cell or progenitor thereof. The shear modulus of the cell culture substrate of the device is in the range of the tissue type to be evaluated. Moreover, cell behavior or response are induced by contact with substrates of varying stiffness. For example, the differentiation path of stem or progenitor cells is driven toward a certain phenotype based on the shear modulus of the substrate upon which the cells are cultured.

These and other capabilities of the invention, along with the invention itself, will be more fully understood after a review of the following figures, detailed description, and claims.

DETAILED DESCRIPTION OF PREFERRED EMBODIMENTS

Embodiments of the invention provide techniques for measuring and characterizing the dynamics of cell traction forces. Tunable elastic gel substrates can be prepared and disposed in multi-well plates. The gels can be of a uniform predetermined thickness. A multi-well plate can be loaded with gels of different stiffness. The gel surfaces within each well can be modified to incorporate extracellular ligands to facilitate cell adhesion within a circular island around the gel center. A cell culture can be placed within the circular island. An array of ring-shaped punch indenters can be attached to a loading platen such that the center of each indenter is aligned with a gel substrate. The indenters can apply tensile or compressive strains to the gel substrates. The magnitude, duration, and frequency of the strain can be controlled by a motor assembly coupled to a control system. The apparatus can be disposed in an incubator for long term cell culture experiments.

The cell culture can be observed while a strain is applied. A ring-shaped indenter can be mounted on a microscope, coaxial to the objective lens, and lowered manually by a calibrated amount onto the underlying gel. The strain can be applied and removed rapidly in a controlled and repeatable manner to simulate physiological ranges. The gel can be of varying thickness. Also, directional stains can be imposed by varying the indenter profile. This apparatus is exemplary, however, and not limiting of the invention as other implementations in accordance with the disclosure are possible.

Figure 1:
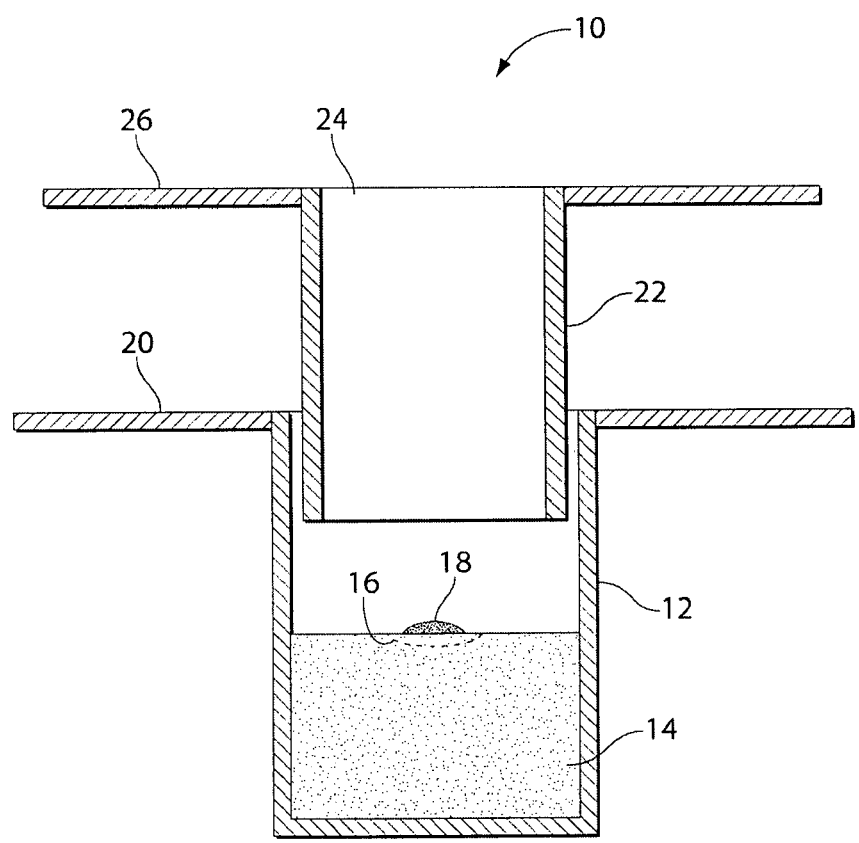
FIG. 1 is a side view of a ring-shaped indenter disposed within a well.

Referring to FIG. 1, a ring-shaped indenter and well assembly 10 is shown. The assembly 10 includes a well 12, a tunable elastic gel substrate 14, a ligand 16, a cell culture 18, an optional plate 20, a ring-shaped indenter 22, an optional opening 24, and an optional loading platen 26. The well 12 can be a multi-well configuration such as a 96-well assembly comprising a 12×8 matrix of wells in a plate 20 (e.g., a MAXISORP 96-well assembly). The well 12 can also be a six well configuration or a 384 well plate. Generally, the well 12 can include standard multi-well plates used to study various biological endpoints under different interventions.

Figure 4:
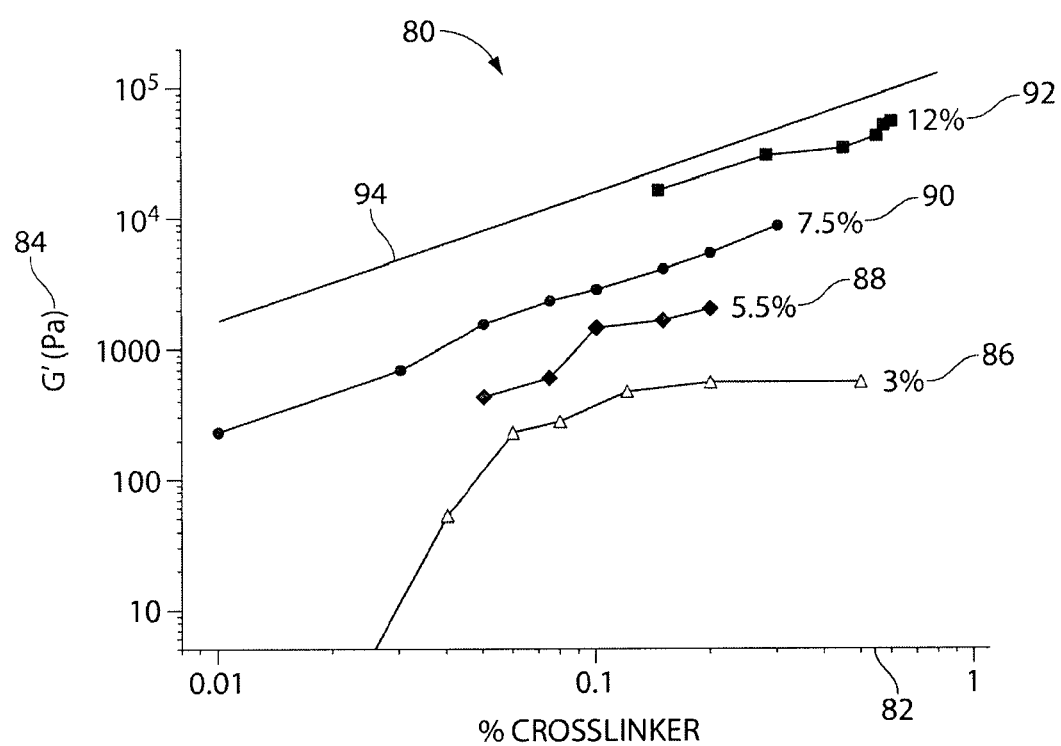
FIG. 4 is a graph depicting the mechanical properties of polyacrylamide substrates.

The tunable elastic polyacrylamide gel substrate 14 can be comprised of variable ratios of acrylamide:bis-acrlamide. As an example, and not a limitation, a gel substrate 14 can be prepared by adding a drop of 0.1M NaOH to the center of 35-mm glass bottomed dish. The dish can air dry overnight. 2-3 drops of 97% 3-aminopropyltrimemethoxylsilane can be added over the NaOH stained circular regions. The dishes are washed, air-dried and 0.5% glutaraldehyde in PBS can be added to the stained region in each dish. The dishes are washed and air-dried overnight. Approximately 10 µl of an acrylamide/bis-acrylamide mixture containing BIS-Acrylamide, Acrylamide, 0.6% of 0.2 µm diameter yellow beads, 0.5% of ammonia persulfate and 0.05% TEMED are added to the center of each dish. Different concentrations of the acrylamide/bis-acrylamide mixture can be used to produce gels of different stiffnesses ranging from 50 to 50,000 Pa. The gel mixture is then covered with plastic cover slips until gelation. The cover slips are removed typically within 30-45 minutes to yield gel substrates with a final thickness of approximately 700 µm. The surface can be activated by adding approximately 200 µl of a solution containing 1 mM sulfosuccinimidyl-6-(4-azido-2-nitrophenylamino)hexanoate dissolved in 200 mM HEPES. The dishes are exposed to ultraviolet light for 5 minutes, washed twice with 0.1M HEPES solution, washed once with PBS, coated with 200 µl of type I Collagen solution (0.1 mg/ml) and stored overnight at 4° C. On the following day, the gels are washed, hydrated with 2 ml of serum free media solution and stored in an incubator at 37° C. and 5% $CO_2$. A 96-well plate, for example, can be loaded with plurality of pre-polymer solutions in different wells. The wells can be covered and cured simultaneously to produce gels of uniform thickness and various shear moduli (e.g., 100, 200, 400, 800, 1600, 3200, 6400, 12800, 25600, and 51200 Pa). For example, referring to FIG. 4, the mechanical properties of exemplary polyacrylamide substrates are plotted on a graph 80. The graph 80 includes a percentage of crosslinker axis 82, and an indication of the shear modulus (G') in Pascal on another axis 84. The shear modulus of polyacrylamide gels with a range of acrylamide to bis-acrylamide proportions can be measured (indicated as percents near data lines 86, 88, 90, 92). The shear modulus 84 increases at constant polymer mass with increasing crosslinker 82. Increasing the concentration of the acrylamide from 3 to 12% (86, 88, 90, 92) creates a stiffness range from approximately 10 to 50,000 Pa. The solid line 94 denotes the theoretical stiffness of a rubber-like network if every cross link was elastically effective.

The surface ligand 16 is generally added to improve cell adhesion to the gel 14. For example, the gel surfaces are treated with a heterobifunctional crosslinker (sulfo-SANPAH), which can covalently link a desired ligand to the gel. Exemplary ligands include extracellular matrix (ECM) proteins such as collagen (type I collagen), laminin, fibronectin or combinations thereof. The cell culture 18 can be human fetal lung fibroblasts (HFL-1) plated at a low-density (e.g., 1000 cells per well) to minimize cell-cell interactions. In general, the cell culture 18 can include any adherent cell type such as cells derived from red blood, nerve, bone, heart, lung, GI tract and adipose stem cells.

As an example, Human Airway Smooth Muscle (HASM) cells can be isolated from tracheal muscle of lung transplant donors. The cells can be cultured on plastic in Ham's F-12 medium supplemented with 10% fetal bovine serum, 100 U/ml of penicillin, 100 mg/ml of streptomycin, 200 mg/ml of amphotericin B, 12 mM NaOH, 1.7 mM CaCl2, 2 mM L-glutamine, and 25 mM HEPES. After the cells reach confluence in plastic dishes, they can be serum deprived for 42 hours to arrest the cell growth cycle in the G1/G0 phases. The cells 18 can then be plated very sparsely (~1,000 cells/dish) in serum-free medium on type I collagen-coated (0.1 mg/ml) polyacrylamide gel 14 dishes 12 for 6 hours before experiments are conducted. The following pharmacological interventions can be used to modulate the CSK filaments and baseline contractility for the specified incubation times: Jasplakinolide (F-actin stabilization, 0.1 µM, 10 min), Latrunculin-A (disruption of F-actin via sequestration of actin monomers, 0.1 µM, 20 min), ML7 (inhibition of myosin light chain kinase (30 μM, 10 min) and TGF-β (10 ng/ml, 5 days). ATP was depleted by incubating cells in PBS with NaN3 (2 mM) and deoxyglucose (10 mM) for 45-60 minutes.

The ring-shaped indenter 22 can be mounted on an optional platen 26 and disposed above the center of the well 12. The inner diameter of the indenter 22 is larger than the cell culture plating area 18, and the outer diameter of the indenter 22 is less than the diameter of the well 12. The indenter 22 can be configured to apply lateral and longitudinal strains on the gel 14. In an embodiment, the indenter 22 includes an opening 24 configured to allow free communication (i.e., fluid flow) between the environment and the cell culture 18. In another embodiment, the indenter 22 is closed (i.e., does not include an opening 24) and therefore inhibits communication between the environment and the cell culture 18.

Figure 2:
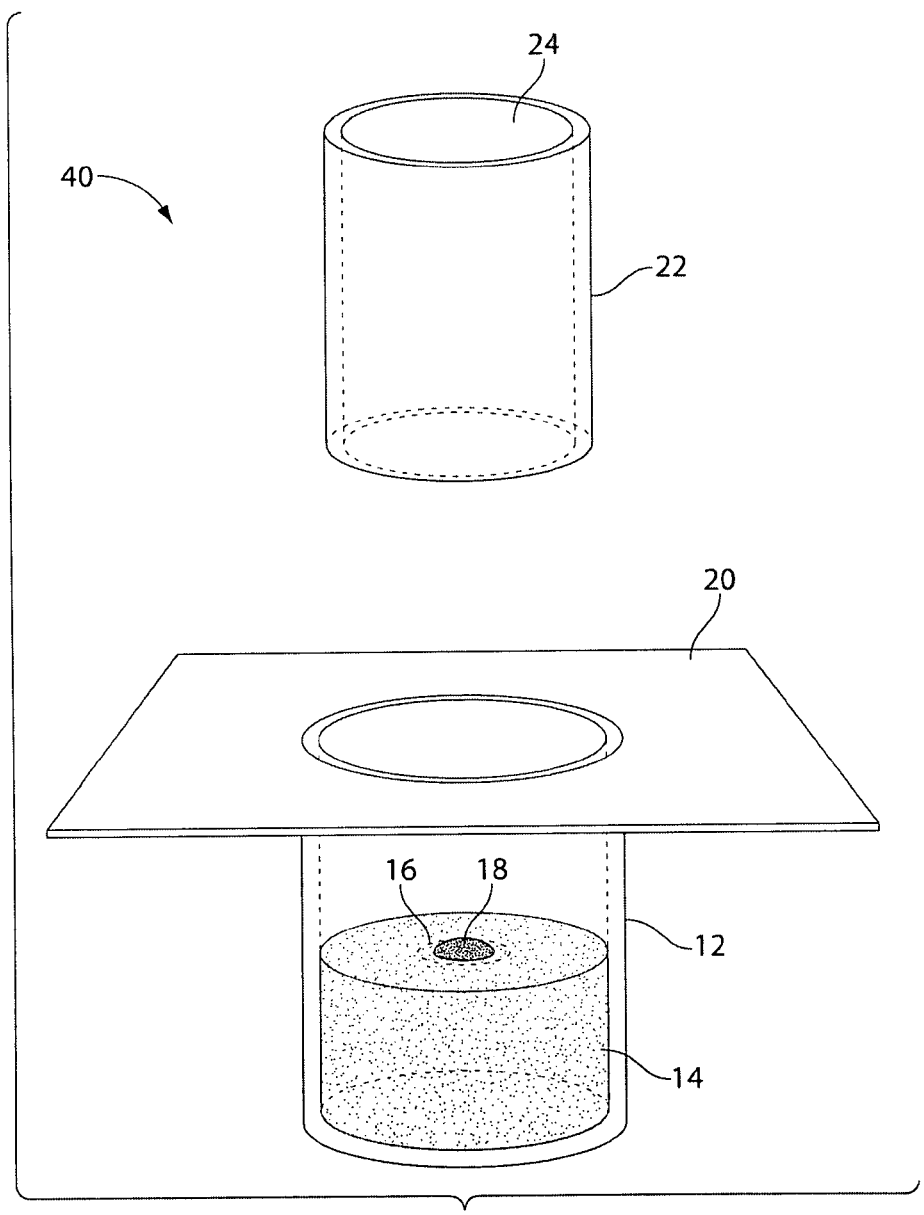
FIG. 2 is a perspective view of a ring-shaped indenter disposed above a well.

Referring to FIG. 2, with further reference to FIG. 1, a perspective view of a ring-shaped indenter and well assembly 40 is shown. The relative size of the indenter 22 as compared to the well 12 is exemplary only, and not limitation. In general, the outer diameter of the indenter 22 is less than the diameter of the well 12, and the inner diameter of the indenter 22 can be approximately the size of the cell culture 18. In an embodiment, the material used to create the indenter 22 is DELRIN®.

Figure 3:
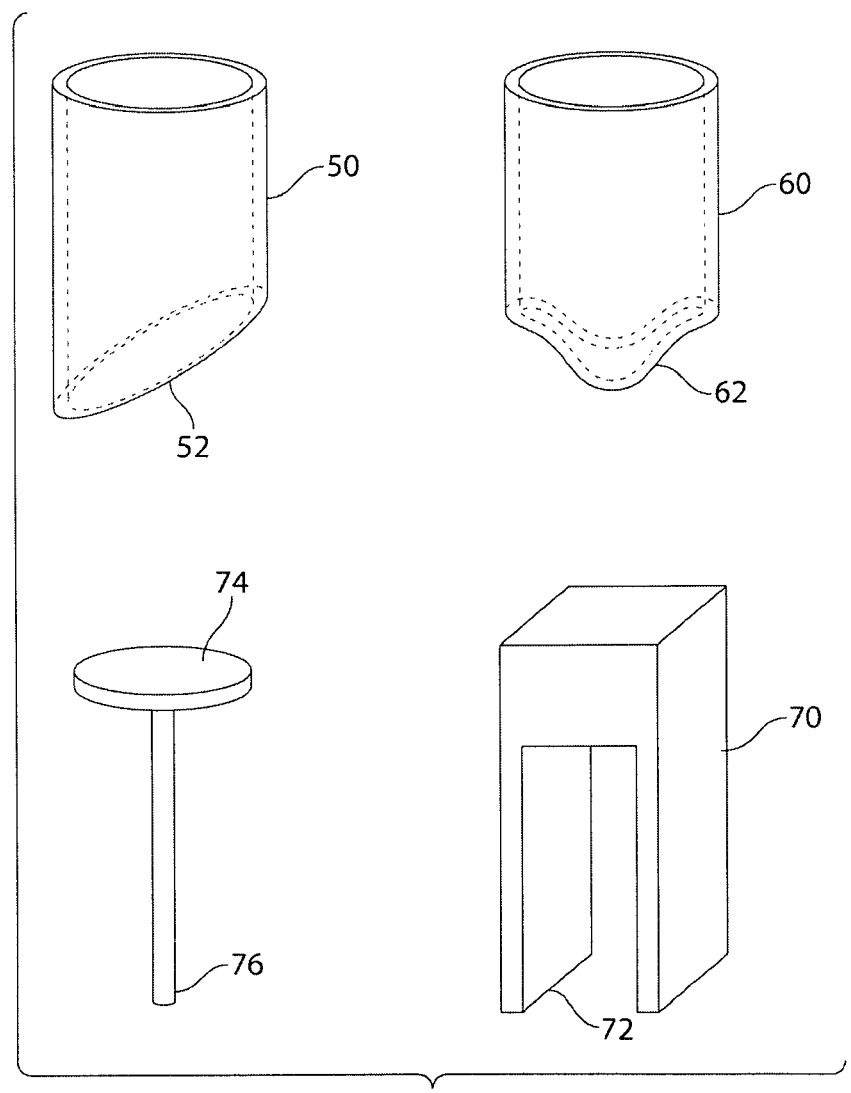
FIG. 3 is a perspective view of exemplary ring-shaped indenters with differing distal ends.

Referring to FIG. 3, with further reference to FIGS. 1 and 2, exemplary ring-shaped indenters 50, 60, 70, 74 are shown. As an example, and not limitation, the indenter 50 includes a angular distal end 52 configured to apply a directional strain on the gel 14. For example, the indenter 50 can be configured to be lowered vertically into a well 12 while simultaneously being displaced in a horizontal axis. The indenter 60 includes a sinusoidal distal end 62 configured to apply a nonlinear strain across the gel 12. In an embodiment, the indenter 70 can be a square or rectangle with prongs 72 configured to impart a strain on the gel 14. In operation, the ring-shaped indenter is not limited to a circular closed geometric ring. In an embodiment, the indenter 74 is a needle with either a blunt or pointed end 76. The needle 74 can be solid or hollow. As illustrated in FIG. 3, the ring-shaped indenter can include open ends with one or more prongs configured to impart a strain across the gel 12. In general, the ring-shaped indenters can be configured with various geometric shapes to impart a strain profile as required by cells being tested and the corresponding test schema.

Figure 5:
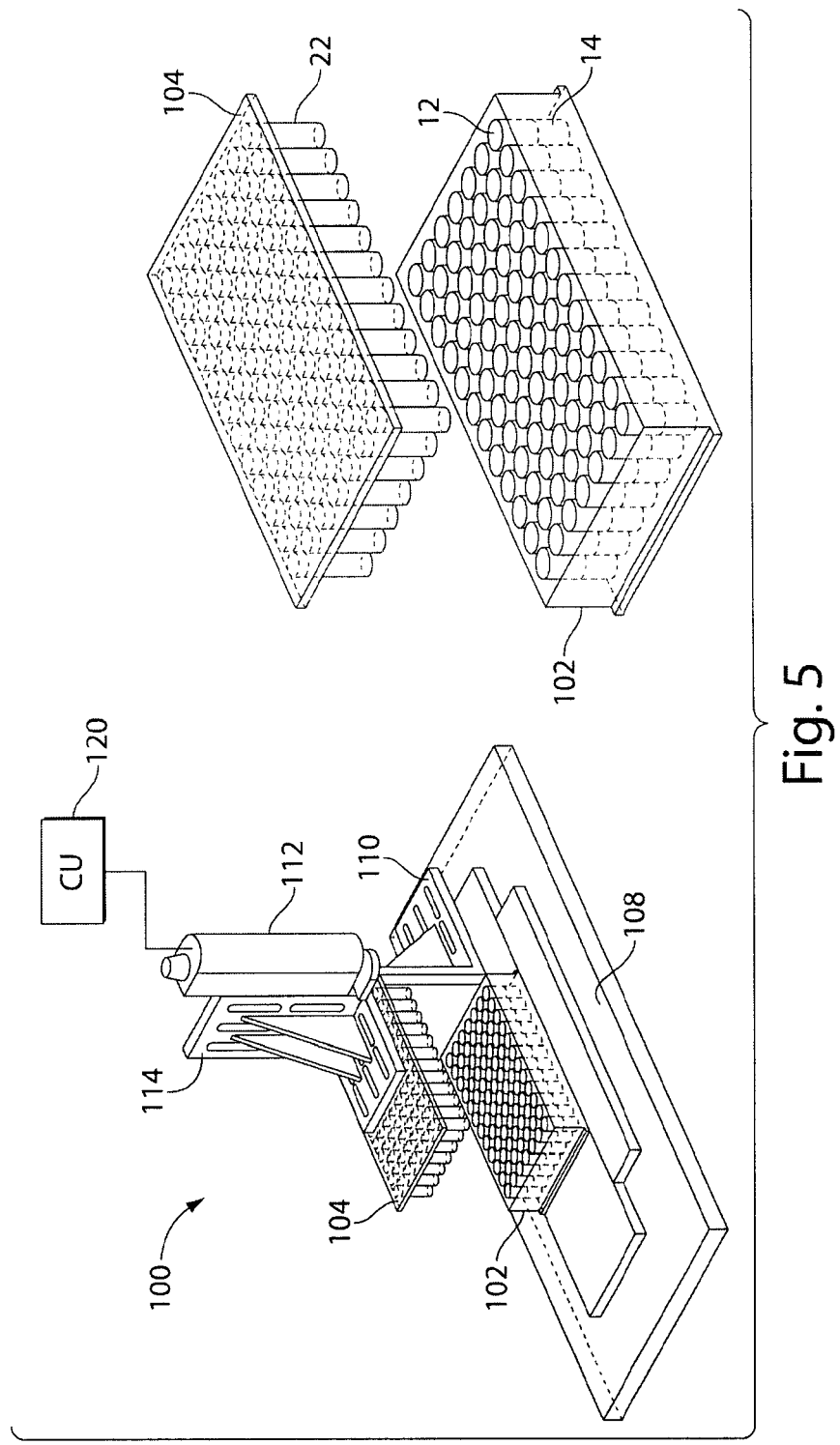
FIG. 5 is a view of an exemplary bio-matrix system in an up position.
Figure 6:
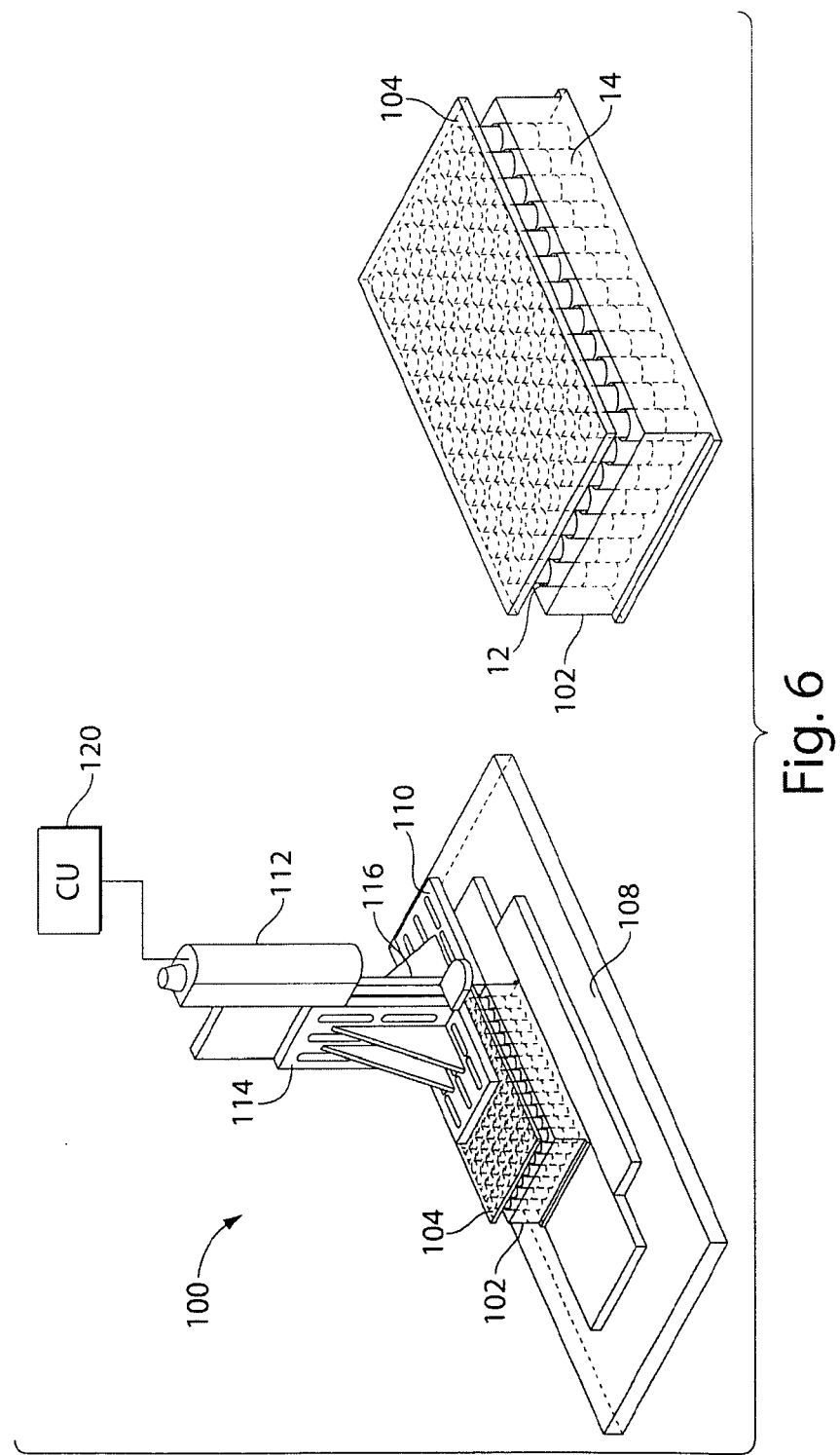
FIG. 6 is a view of an exemplary bio-matrix system in a down position.
Figure 13:
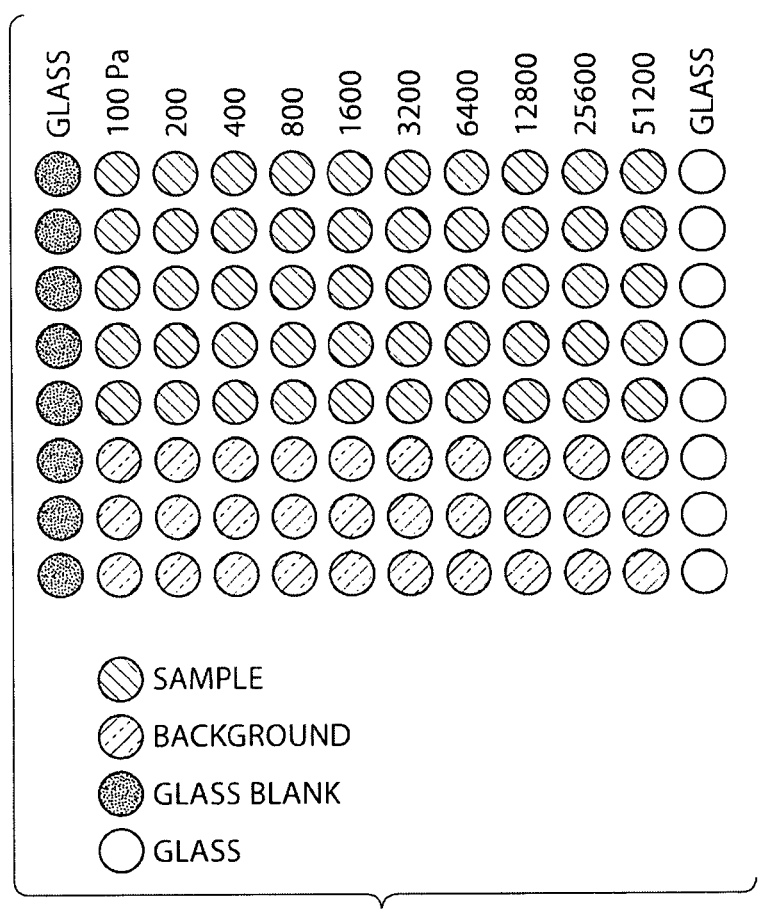
FIG. 13 is a exemplary 96-well plate configured with a plurality of polyacrylamide substrates.

Referring to FIGS. 5 and 6, with further reference to FIG. 1, a bio-matrix stretch system 100 is shown. The system 100 includes a 96-well plate 102 including 96 wells 12, each well with a tunable elastic gel 14, a loading platen 104 including 96 ring-shaped indenters 22, a stage table 108, an X-Y stage 110, a Z-drive motor 112, an indenter bracket 114, a lead screw 116, and a control unit 120. As an example, and not limitation, the well plate 102 includes 96 wells and the loading platen in 104 includes 96 indenters. Other plate sizes and configurations are within the scope of the invention (e.g., 6, 12, 144, 384). Referring to FIG. 13, with further reference to FIG. 4, in an embodiment, a 96-well plate can be configured so the stiffness of the elastic gel 14 in each of the wells 12 varies columnwise. Further, a non-derivatized gels can serve as a background control for each stiffness value.

The stage table 108 provides a base for the system 100. For example, the system 100 can be portable in that the base 108 can be affixed to a cart, microscope stage or a shelf within an incubator. The stage 110 can include motion actuators and sensors configured to move the platen 104 along the X and Y axes (i.e., horizontally). In general, a stage 110 can include encoders configured to resolve movement on the order of microns (e.g., Newport Corp., ULTRALIGN series products). The Z-drive motor 112 is configured to move the platen 104 along the Z axis (i.e., vertically). For example, the Z-drive motor can be a stepper motor or a piezoelectric actuator. In an embodiment, the Z-drive can be a lead screw 116 connected with the bracket 114. The Z-drive can also be a linear or hydraulic piston. In an embodiment the indenter bracket 114 can include a rotary actuator to allow for pitch and roll control of the platen 104. Further, the bracket 114 can include an orbit actuator configured to allow the platen 104 to move in a circular manner within the X-Y plane.

The control unit 120 is operably connected to the motion actuators and sensors (e.g., 110, 112, 114). In an embodiment, the control unit 120 can be a personal computer including a processor, memory, input and output devices. In general, the control unit 120 can receive and execute computer-readable instructions contained within a computer-readable medium. Computer-readable medium can include floppy disks, hard disks, CD-ROMS, flash ROMS, nonvolatile ROM, RAM, and downloadable files. For example, the control unit 120 can be a laptop computer running the LABVIEW data acquisition software (National Instruments, Austin Tex.). The control unit 120 can be programmed to incorporate a range of loading magnitudes (0-20% strain), durations and frequencies. For example, strains can be applied in different waveforms (e.g., square, triangular, sinusoidal) and at varying frequencies (most typically between 0.05 and 10 Hz). The control unit 120 can be customized to exert graded loading (by varying indention depths) with various time course of deformation. In an example, referring to FIG. 7, an experimental protocol 200 for dynamic traction measurements is shown. The protocol includes a time component 202, and a strain component 204. Following a brief period of no-load 206, test cells can be subjected to a single transient stretch of 4 seconds duration 208 followed by a return to zero strain 210. This programmable control can test a variety of cell types and different cell media constituents, which can be varied independently in each well of the 96-well plate, for example.

The control unit 120 can be included on a network (e.g., LAN, WAN, Internet) and configured to send and receive information across the network. For example, the bio-matrix system 100 can be one of several systems connected to a larger distributed control structure.

Figure 8:
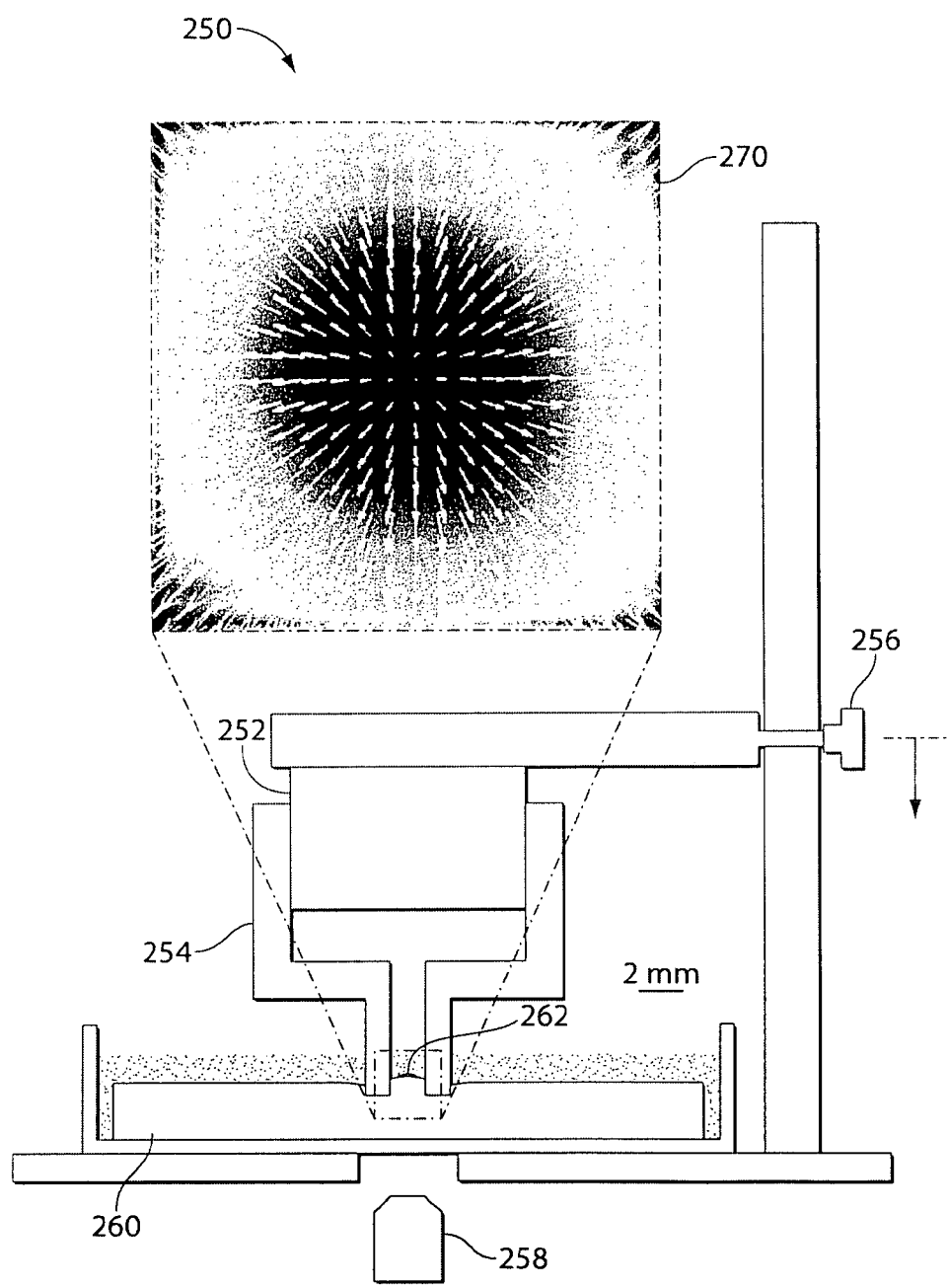
FIG. 8 is a system diagram of a microscope and ring-shaped indenter assembly.

Referring to FIG. 8, a microscope system 250 is shown. The microscope includes an objective lens 258, an indenter 254, a condensing lens 252, a calibrated vertical displacement control 256, a tunable elastic gel 260, and a cell culture 262. In general, the indenter 254 can be mounted coaxial with the objective lens 258, and is configured to allow viewing of the cell culture 262. The displacement control 256 is mechanically coupled to the indenter 254 and is configured to move the indenter 254 such that it can impart a strain on the gel 260. In an embodiment, the displacement control 256 is the objective lens focal control knob, such that the indenter 254 is lowered onto the gel 260. In another embodiment, the displacement control can be an electro-mechanical apparatus (e.g., stepper motor, encoder, and control system) and can be configured to move the indenter 254. The cell culture 262 includes cells previously incubated within a well of the bio-matrix system 100 (i.e., cell culture 18). In an embodiment, a well 12 from the bio-matrix system 100 can be viewed directly with the microscope system 250 (i.e., the gel 260 is the gel 14). In operation, the indenter 254 imparts a strain on the substrate 260. In general, the level of the strain is proportional to the depth the indenter travels down onto the gel 260. For example, the displacement strain of the gel 260, in the area around the end of the indenter 254, is illustrated in chart 270.

Figure 9:
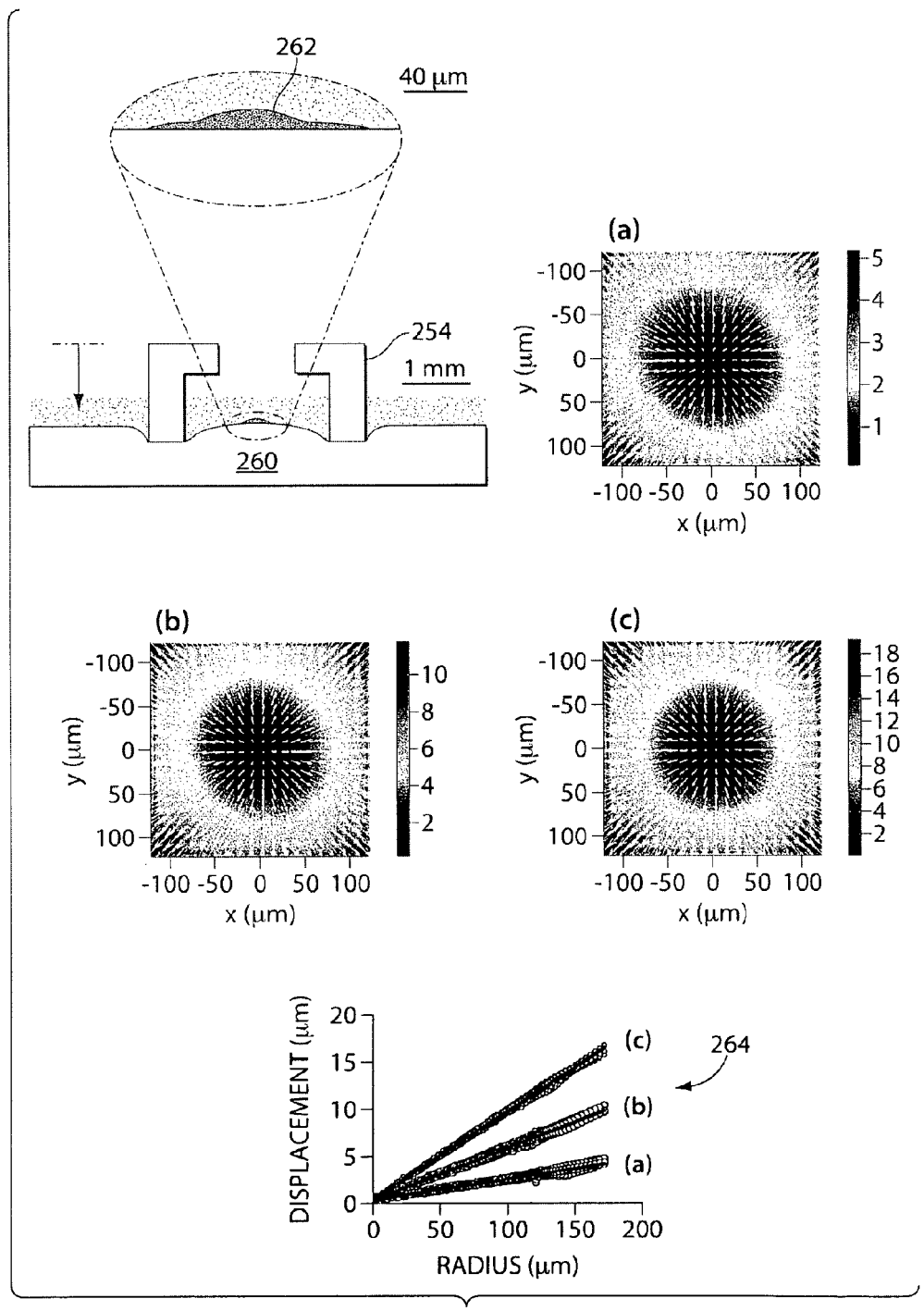
FIG. 9 is a conceptual diagram of a longitudinal strain placed on a cell culture.

Referring to FIG. 9, with further reference to FIG. 8, a conceptual diagram of a longitudinal strain placed on the cell culture 262 is shown. Pre-defined deformations can be imposed upon cells cultured on elastic polyacrylamide substrate 260 using a ring-shaped punch indenter 254 of the microscope system 250. The indenter 254 is mounted to the microscope, coaxial to the objective lens, and lowered manually by a calibrated amount onto the underlying substrate 260. Direct measurements of displacements can be observed through the use of fluorescent bead markers embedded within the gel 260, and finite element analysis of gel deformation, to map strain fields corresponding to prescribed indentation depths. The resulting strain field in the vicinity of the cell culture 262 is generally isotropic in the plane and uniform. The deformation field can be applied and removed rapidly, and, by using indentations of defined depth, can create controlled and repeatable cell strains that span the physiological range. For example, ring-shaped punch indentation of a 0.7 mm thick elastic substrate using an indenter 254 with an inner diameter of 2 mm and an outer diameter of 3 mm causes the substrate to stretch as depicted in the displacement field maps labeled (a), (b) and (c) and strain chart 264. The displacement vectors in charts (a), (b) and (c) are scaled by a factor of 4 for clarity. Despite different maximum displacement magnitudes in (a), (b) and (c), the corresponding strain field is homogenous and uniform in the plane. In general, for a particular indenter size (e.g., inner and outer diameter) and indentation depth, the applied strains can be modified from a tensile to a compressive field by varying the gel thickness.

Figure 10:
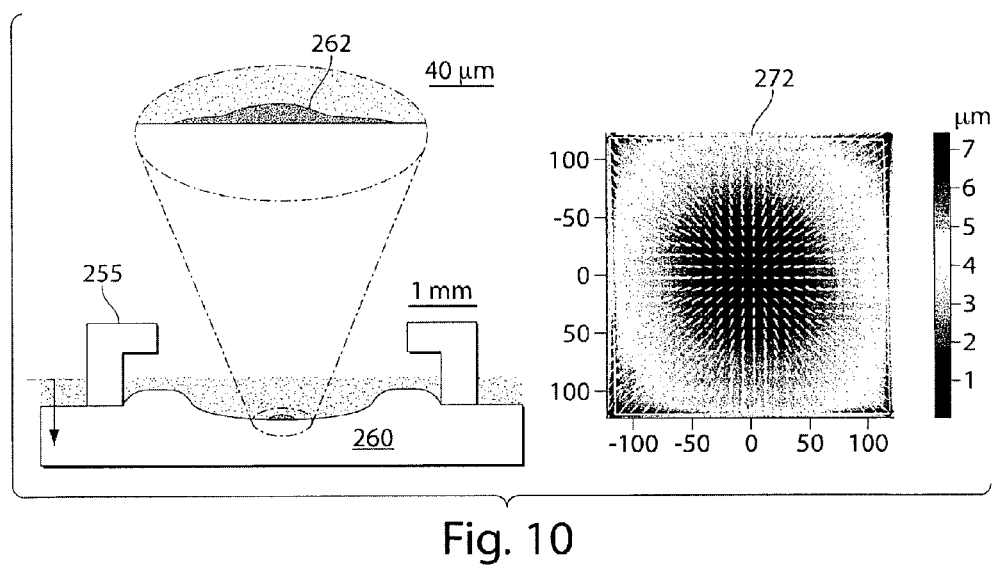
FIG. 10 is a conceptual diagram of a compression strain placed on a cell culture.

Referring to FIG. 10, with further reference to FIGS. 8 and 9, a conceptual diagram of a compression strain placed on a cell culture 262 is shown. The diagram includes a cell culture 262, a tunable elastic substrate 260, and a ring-shaped indenter 255. For example, the elastic substrate 260 can be 0.7 mm thick, and the indenter 255 has an inner diameter of 4 mm and an outer diameter of 6 mm, and causes the substrate 260 to compress. The measured gel displacement field image 272 represents the central region (200×200 µm) corresponding to a particular indentation depth. The arrows on the image 272 are scaled by a factor of 2 for clarity. In general, the corresponding compressive strain field is homogenous and uniform in the plane.

Figure 11:
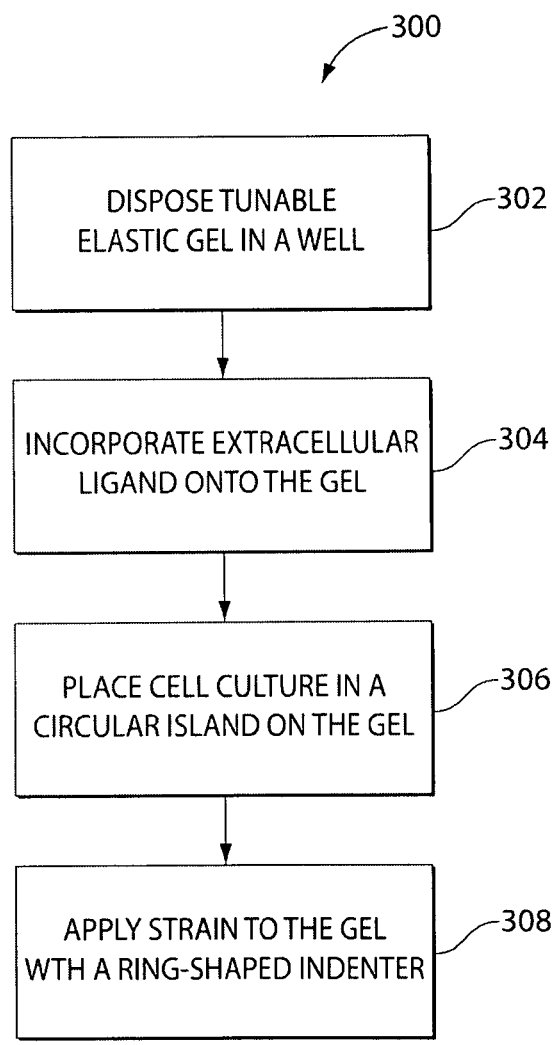
FIG. 11 is a process flowchart of a method to apply a strain to a cell culture disposed on a tunable elastic gel.

In operation, referring to FIG. 11, with further reference to FIG. 5, a process 300 to apply a strain to a cell culture disposed on a tunable elastic gel with the bio-matrix system 100 includes the stages shown. The process 300, however, is exemplary only and not limiting. The process 300 may be altered, e.g., by having stages added, removed, or rearranged.

At stage 302, a tunable elastic gel 14 is disposed in a well 12. For example, gels 14 of a uniform and predetermine thickness can be affixed firmly to the bottom of a 96-well plate. The stiffness of the gel 14 in each of the wells can vary based on the type of cell culture 18 to be tested and the nature of the experiment.

At stage 304, the gel surfaces within each well 12 can be modified to incorporate extracellular matrix ligands such as collagen or fibronectin to facilitate cell 18 adhesion within a circular island around the gel 14 center. At stage 306, a cell culture 18 is placed on the gel 14.

At stage 308, a strain is applied to the gel 14 with an array 104 of ring-shaped indenters 22. In general, the indenters 22 have inner diameters slightly larger than the size of circular cell islands 18. The indenters 22 can be attached to a loading platen 104 with their centers aligned to the center of gel substrates 14. The loading platen 104 is mounted to a stage assembly 110, 112, 114 and precise micron scale movements can be prescribed using a commercially available linear actuator (i.e., control unit 120). In an example, data acquisition and control is performed via a laptop computer running the LABVIEW data acquisition software. The entire bio-matrix system 100 can be fixed in an incubator for long term cell culture. The bio-matrix system 100 can incorporate a range of physiological substrate stiffnesses (50 Pa to 40 kPa), loading magnitudes (0-20% strain), durations and frequencies. It can be customized to exert gradients in loading (by varying indentation depths), test a variety of cell types and different cell media constituents, which all can be varied independently in each well of the 96-well plate.

Figure 7:
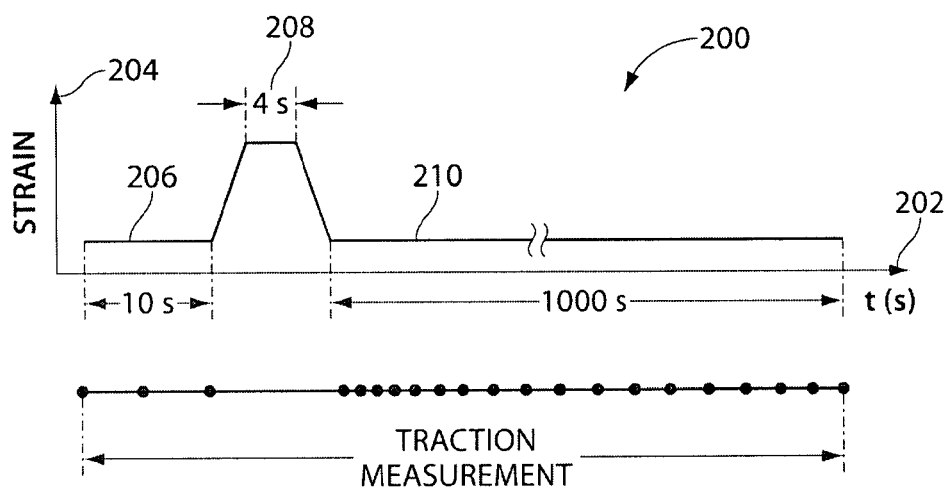
FIG. 7 is a diagram of an experimental protocol for dynamic cell traction measurements.
Figure 12:
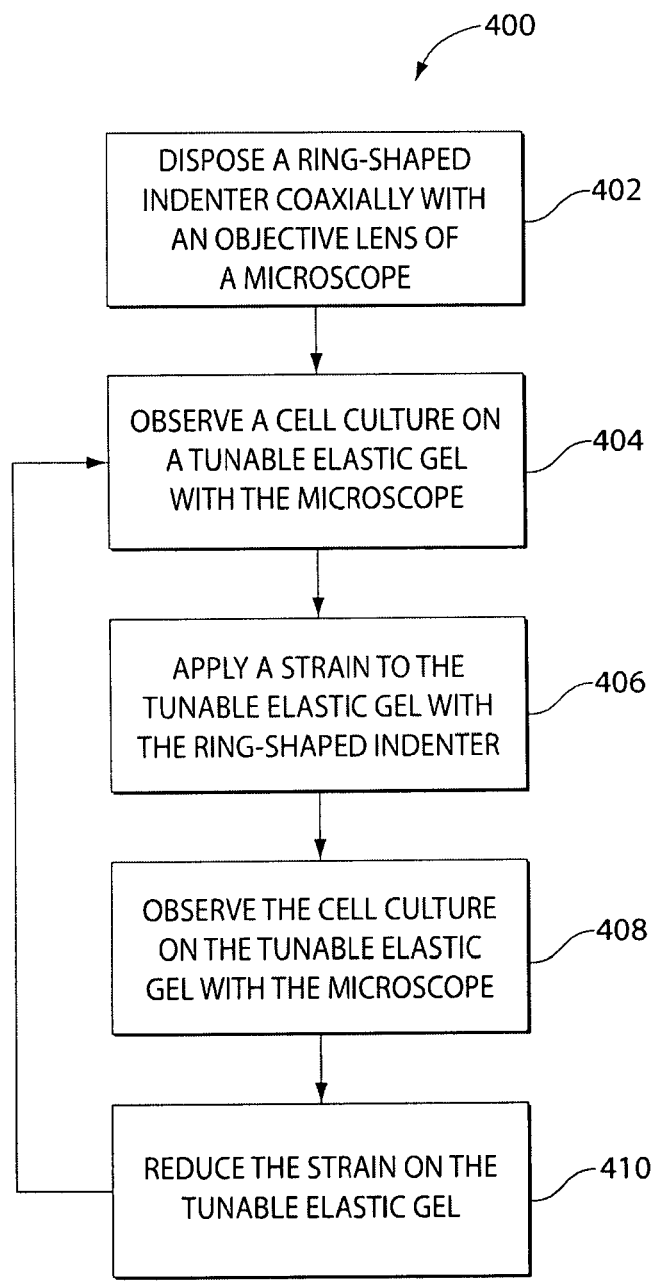
FIG. 12 is a process flowchart of a method to observe changes in the fraction force a cell exerts upon a tunable elastic matrix.

In operation, referring to FIG. 12, with further reference to FIG. 7, a process 400 to observe changes in the traction force a cell exerts upon a tunable elastic matrix using the microscope system 250 includes the stages shown. The process 400, however, is exemplary only and not limiting. The process 400 may be altered, e.g., by having stages added, removed, or rearranged.

At stage 402, a ring-shaped indenter 254 can be disposed on a microscope. In an embodiment, the indenter 254 is adjustably mounted and can be configured to impart a strain on the gel 260. In another example, the indenter 254 is coupled to a control system configured to apply cyclical strains on the gel 260. The diameter of the indenter 254, 255 can be changed to exert a compression or a tensile strain on the gel 260 within the cell culture island 262.

The cell culture 262 can be observed at stage 404. For example, the cell culture 262 can be a portion, or all, of the cells 18 cultured in the bio-matrix system 100 on the tunable gels 14. In an embodiment, a 96-well plate can be transferred from the bio-matrix system 100 to the microscope system 250.

At stage 406, pre-defined deformations can be imposed upon cells 262 cultured on elastic polyacrylamide substrate 260 using the ring-shaped punch indentation system 250. The deformation field can be applied and removed rapidly, and, by using indentations of defined depth, can create controlled and repeatable cell strains that span the physiological range. For example, for a particular indenter size and indentation depth, the applied strains can be modified from a tensile to a compressive field by varying the gel 260 thickness.

At stage 408, the cell culture 18 can be observed while under the strain applied by the ring-shaped indenter. The amount of strain can be based on manual adjustments to the displacement control 256. In another embodiment, the strain can be applied via a control system coupled to the indenter 254.

At stage 410, the strain placed on the gel 14 can be reduced or removed based on the position of the indenter 22 relative to the gel 14. The cell culture 18 can thus be observed in the relaxed state at stage 404.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:
1. An apparatus comprising:
a closed-bottom well;
a tunable elastic substrate disposed within the closed-bottom well, the tunable elastic substrate having a cell plat- ing side and a second side affixed to a bottom of the closed-bottom well, the tunable elastic substrate comprising a gel;
a cell plating area disposed on a cell plating side of the tunable elastic substrate; and
a ring-shaped punch indenter with an inner diameter that is larger than the size of the cell plating area, and an outer diameter that is smaller than a diameter of the closed-bottom well, wherein the ring-shaped punch indenter is configured to indent into the gel on the cell plating side to a depth thereby compressing the tunable elastic substrate between the indenter and the bottom of the closed-bottom well.

2. The apparatus of claim 1 further comprising at least one motor assembly operably coupled to the ring-shaped punch and configured to move the ring-shaped punch within the well.

3. The apparatus of claim 2 wherein the ring-shaped punch is configured to move vertically with respect to the tunable elastic substrate.

4. The apparatus of claim 2 wherein the ring-shaped punch is configured to move horizontally with respect to the tunable elastic substrate.

5. The apparatus of claim 2 further comprising a programmable control system configured to control the at least one motor.

6. The apparatus of claim 1, further comprising a plurality of additional wells and a plurality of additional ring-shaped punch indenters such that each additional indenter is disposed within one of the additional wells.

7. The apparatus of claim 6 wherein each of the plurality of additional wells has disposed therein the tunable elastic substrate.

8. The apparatus of claim 7 wherein the tunable elastic substrate in a well is of a first thickness, and the tunable elastic substrate in another well is of a second thickness.

9. The apparatus of claim 7 wherein the tunable elastic substrate in a first well is of a first stiffness, and the tunable elastic substrate in a second well is of a second stiffness.

10. The apparatus of claim 1 wherein the well is a 96-well plate and the ring-shaped punch indenter comprises 96 ring-shaped punch indenters such that each indenter is disposed within each of the wells.

11. The apparatus of claim 1, wherein said cell plating area comprises a ligand.

12. The apparatus of claim 1, wherein said cell plating area comprises type I collagen.

13. The apparatus of claim 1, wherein said cell plating area comprises an extracellular matrix protein.

14. The apparatus of claim 13, wherein said protein comprises collagen, fibronectin, laminin, or a combination thereof.

15. The apparatus of claim 1, wherein said substrate comprises polyacrylamide.

16. The apparatus of claim 1, wherein said apparatus comprises a multi-well plate.

17. The apparatus of claim 16, wherein said multi-well plate comprises six wells.

18. The apparatus of claim 16, wherein said multi-well plate comprises 384 wells.

19. The apparatus of claim 1, wherein said substrate comprises 3-12% acrylamide.

20. The apparatus of claim 1, wherein said substrate comprises a shear moduli ranging from 10-50,000 Pa.

21. The apparatus of claim 1, wherein said substrate comprises a shear moduli selected from the group consisting of 100, 200, 400, 800, 1600, 3200, 6400, 12800, 25600, and 51200 Pa.

22. The apparatus of claim 1, wherein said substrate comprises fluorescent bead markers.

23. The apparatus of claim 1, wherein the closed-bottom well includes a glass bottom.

24. The apparatus of claim 1, wherein the elastic tunable substrate has a shear moduli between 100 and 1000 Pa.

* * * * *

UNITED STATES PATENT AND TRADEMARK OFFICE
CERTIFICATE OF CORRECTION

PATENT NO. : 8,993,312 B2  
APPLICATION NO. : 12/675882  
DATED : March 31, 2015  
INVENTOR(S) : Krishnan et al.

Page 1 of 1

It is certified that error appears in the above-identified patent and that said Letters Patent is hereby corrected as shown below:

In the Specification

Delete the paragraph beginning at Column 1, Line number 14 and replace it with the following paragraph:
This invention was made with government support under HL082856, GM073628, and HL088028 awarded by the National Institutes of Health. The government has certain rights in the invention.

Signed and Sealed this
Fourteenth Day of January, 2025

Derrick Brent
*Acting Director of the United States Patent and Trademark Office*